(12) United States Patent
Dmuschewsky

(10) Patent No.: US 9,814,529 B2
(45) Date of Patent: Nov. 14, 2017

(54) INSTRUMENT HOLDER AND GRIP FOR A MEDICAL, PARTICULARLY A SURGICAL, INSTRUMENT

(71) Applicant: Waldemar Link GmbH & Co. KG, Hamburg (DE)

(72) Inventor: Klaus Dmuschewsky, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 435 days.

(21) Appl. No.: 14/406,104

(22) PCT Filed: May 24, 2013

(86) PCT No.: PCT/EP2013/060730
§ 371 (c)(1),
(2) Date: Dec. 5, 2014

(87) PCT Pub. No.: WO2013/186027
PCT Pub. Date: Dec. 19, 2013

(65) Prior Publication Data
US 2015/0127007 A1    May 7, 2015

(30) Foreign Application Priority Data
Jun. 11, 2012    (EP) .................................... 12171416

(51) Int. Cl.
*A61B 19/00* (2006.01)
*A61B 17/16* (2006.01)
(Continued)

(52) U.S. Cl.
CPC .......... *A61B 19/26* (2013.01); *A61B 17/1659* (2013.01); *A61B 17/1668* (2013.01);
(Continued)

(58) Field of Classification Search
CPC ......... A61B 19/00; A61B 17/16; A61B 19/26; A61B 17/1659; B25G 1/00
See application file for complete search history.

(56) References Cited

U.S. PATENT DOCUMENTS 6,205,884 B1 * 3/2001 Foley ................. A61B 17/1659 606/85
6,663,636 B1 * 12/2003 Lin ..................... A61B 17/1659 606/79

(Continued)

FOREIGN PATENT DOCUMENTS

DE    19501882    11/1995
DE    29807671    9/1999

*Primary Examiner* — Christopher Beccia
(74) *Attorney, Agent, or Firm* — Sand & Sebolt

(57) ABSTRACT

An instrument holder and grip for detachably connecting to a medical instrument, which has a basic body with a grip section and a connecting section for connecting to the medical instrument. A locking means movable from a release position into a locking position is provided in the connecting section for locking the medical instrument on the connecting section. The instrument holder and grip has lever elements connected together and each mounted pivotably on the basic body. A first element has an actuating lever arm and a second element moves the locking means. The holder permits significantly simplified cleaning and sterilization after use, while continuing to provide a reliable holding effect on the instrument. It is possible to dismantle the instrument holder into a few easily cleaned parts with a few simple actions and without small parts such as connecting pins or similar.

23 Claims, 4 Drawing Sheets

(51) Int. Cl.
*B25G 1/00* (2006.01)
*A61B 90/50* (2016.01)
*A61B 17/00* (2006.01)

(52) U.S. Cl.
CPC ............... *A61B 90/50* (2016.02); *B25G 1/00* (2013.01); *A61B 2017/0046* (2013.01)

(56) References Cited

U.S. PATENT DOCUMENTS

2008/0255565 A1 10/2008 Fletcher
2010/0331902 A1 12/2010 Biegun

* cited by examiner

INSTRUMENT HOLDER AND GRIP FOR A MEDICAL, PARTICULARLY A SURGICAL, INSTRUMENT

TECHNICAL FIELD

The present invention relates to a tool holder and grip for detachably connecting to a medical, particularly surgical, tool, having the features of a basic body with a grip section and a connection section for connecting to the medical tool, wherein a locking means which can be moved from a release position into a locking position is provided in the connection section for locking a medical tool that is to be placed on the connection section, wherein the tool holder and grip further has a lever arrangement of lever elements which are connected to one another and are each mounted pivotably on the basic body, of which lever elements a first has an actuating lever arm and a second moves the locking means, said locking means being formed in particular on a lever arm of this lever element.

PRIOR ART

It is known to form medical instruments, particularly surgical instruments, from elements of a grip part and a holder part as well as the actual tool part, that can be detachably connected to one another. This is particularly advantageous since in this way different tool parts, for example differently shaped tool parts or differently functioning tool parts, can be connected to a universal grip and holder in order to form different medical instruments.

In this case, the tools on the tool holder and grip must on the one hand be able to be exchanged quickly and easily, but on the other hand must be securely connected to the tool holder and grip during use. Known examples of such instruments, in which the tools are described as bone rasps, are specified in the documents DE 195 01 882 C2 and DE 298 07 671 U1. In the solution disclosed in the first-mentioned document, an attachment and locking takes place via a retaining pin, provided with a star-shaped extension, on the tool part, which is guided along the tool holder and grip in an orientation rotated in relation to the normal direction with the rays of the star between corresponding protrusions of a receiving channel in the tool holder and grip and then is rotated through a certain angle into the position of use. In this position, the protrusions in the retaining channel engage behind the star-shaped extensions at the end of the retaining pin. As additional locking, a spring-loaded locking bolt moves into a corresponding recess on the tool, in order to prevent inadvertent reverse rotation and release of the tool.

In the example of the second-mentioned document, the connection between the tool holder and grip and the tool itself takes place in a connection section which runs at an angle in relation to a longitudinal direction of the tool and also of the holder and grip. A locking pin, which can be moved by means of a slide and extends and is movable along the longitudinal direction of the tool holder and grip, is driven, with the retaining pin running at an angle to the longitudinal direction thereof and being pushed into a correspondingly angled aperture on the grip, into a corresponding locking opening in said pin and thus locks the tool.

Another example of a tool holder and grip, which is known from the prior art and from which the invention here proceeds, is disclosed in U.S. Pat. No. 6,663,363 B1. Therein, a locking means is provided in the form of an extension which is arranged on a lever element and which can be pivoted via a lever arrangement between a release position and a locking position, in which the locking means engages in a recess of a connecting pin of the tool, which is inserted in a receiving opening on the holder and grip, and an open position, in which the locking means releases the pin. The lever arrangement consists in this case of a total of three lever elements, of which a first carries the locking means, a second represents a connecting strut for transmitting the lever force, and a third comprises an actuating lever arm. Thus, by pivoting the actuating lever arm, a force is exerted on the lever element carrying the locking means and pivots or moves this between the locking position and the release position.

One thing that all the previously known solutions have in common is that they produce a secure and reliable attachment of the tool to the tool holder and grip and thus enable reliable and safe use of the instrument thus formed. However, the solutions described above are capable of improvement since they bring certain obstacles and difficulties with regard to a cleaning and sterilization that is necessary after use. This is because, during typical surgical use of a medical instrument that is formed from the tool and the tool holder and grip, it is typically not just the tool itself that is contaminated, but also the tool holder and grip. This contamination comprises in particular blood and tissue residues, and possibly also bone dust or contamination with body fluids other than blood. Since these objects are conventionally reusable instruments or parts, they must, after use, be carefully cleaned of the adhering contamination and sterilized in order thus to avoid any transfer of diseases or any immune reactions brought about as a result of introducing foreign tissue parts or body fluids into the body system of a further patient.

During such cleaning operations that have to be performed, it is particularly difficult to deal with narrow intermediate spaces or cavities like those that exist on the designs known from the prior art. In the tool holder and grip known from DE 195 01 882 C2, this is in particular the blind bore in which the locking pin is arranged and the slot through which the grip part of this locking pin projects. In the element known from DE 298 07 671 U1, it is the entire guide of the locking bar. In the tool holder and grip known from U.S. Pat. No. 6,663,636 B1, it is the receiving space in which the individual lever elements are arranged and in particular the regions between the lever elements and the wall of the grip. This is particularly due to the fact that said instruments are not configured such as to be able to be further broken down into their elements, which applies in particular also to the tool holder and grip disclosed in U.S. Pat. No. 6,663,636 and in particular to the lever arrangement therein. In said document, the individual elements of the lever arrangement are connected to one another and are mounted on the basic body of the tool holder and grip via bearing pins which are not intended to be broken down. Although in theory these retaining pins could be removed and thus the tool holder and grip could be configured such as to be able to be broken down, this would give rise to a large number of small parts which make the breakdown and assembly more difficult for the medical assistants and moreover could be lost. With such small parts, there is also always the risk that they will detach during surgical use of the instrument and will remain in a surgical wound.

DESCRIPTION OF THE INVENTION

The object of the present invention is to remedy this and to further develop a tool holder and grip of the type mentioned in the introduction, such that it permits much easier cleaning and sterilization after use while continuing to hold the tool reliably, and to this end can be broken down, in particular using a few simple motions, into a few easily cleanable parts, without any small parts such as connecting pins or the like.

This object is achieved by a tool holder and grip for detachably connecting to a medical, particularly surgical, tool, having the features of a basic body with a grip section and a connection section for connecting to the medical tool, wherein a locking means which can be moved from a release position into a locking position is provided in the connection section for locking a medical tool that is to be placed on the connection section, wherein the tool holder and grip further has a lever arrangement of lever elements which are connected to one another and are each mounted pivotably on the basic body, of which lever elements a first has an actuating lever arm and a second moves the locking means, said locking means being formed in particular on a lever arm of this lever element; where the lever arrangement is formed of two lever elements which, by virtue of pivot bearing sections formed thereon, are each arranged directly and removably, and in such a way as to be able to pivot with respect to the basic body, on pivot bearing structures formed in the basic body, and each have a bearing connection section on one of their lever arms, which bearing connection sections are connected to one another in a detachable and direct manner and work together to form a connection pivot bearing for the two lever elements, which is movable relative to the basic body. Advantageous further developments of such a tool holder and grip include that the bearing connection section on one of the lever elements has a circular cylindrical section which runs with its longitudinal direction transverse to the direction of extension of the lever arm on which it is arranged, and is fixed to said lever arm, in particular is formed in one piece therewith, and in that the bearing connection section on the other of the lever elements comprises a receiving fork, which is formed in a fork base with a radius corresponding to a radius of the circular cylindrical section and is delimited by lateral legs. The legs of the receiving fork are of unequal length, wherein the leg that transmits force during a closing movement of the lever arrangement, which the latter executes when moving the locking means into the locking position, is the longer leg. The legs of the receiving fork have at their free ends an opening width that is smaller than the diameter of the circular cylindrical section, and in that one of the legs, in particular the shorter leg, is configured as a spring tongue. Furthermore, one of the lever arms of the lever elements on which the bearing connection sections are arranged, in particular the lever arm provided with the bearing connection section of the second lever element, which moves the locking element, is configured as a spring arm with a spring elasticity in a direction transverse to its longitudinal extension. Still further, the lever arm configured as a spring arm runs in a curved manner in a direction opposite to the force which, during a closing movement of the lever arrangement, which the latter executes when moving the locking means into the locking position, force acting thereon. The pivot bearing sections, which are detachably connected in the connection pivot bearing, and the lever elements are configured in such a way that, in the event of an overextension of the lever arrangement, in particular during an opening movement thereof, which the latter executes when moving the locking means into the release position, the pivot bearing sections can be separated and detached from one another by overcoming a retaining force. Furthermore, a circular cylindrical section, formed as a bearing section on at least one lever element, for pivotably mounting the lever element in a receiving channel of the basic body, which receiving channel forms the pivot bearing structure and has a channel base that is curved in a radius corresponding to the radius of the circular cylindrical section. The tool holder and grip may include a U-shaped bearing channel which is formed as a bearing section in at least one of the lever elements and has a channel base curved in a radius for pivotably mounting the lever element on a bearing pin which forms the pivot bearing structure, is fixedly arranged on the basic body and has a radius corresponding to the radius of the channel base. The tool holder and grip may also include an at least partially continuous receiving slot, formed in a section of the basic body, for at least partially receiving the lever elements, wherein the pivot bearing structures for pivotably mounting the lever elements are arranged in the receiving slot. A stop means may be arranged on the actuating lever arm and/or on the basic body for limiting a lever travel of the actuating lever arm in a closing direction in which the locking means is moved into the locking position. The lever elements are each two-armed lever elements), wherein the first lever element has the one actuating lever arm as the first lever arm and has, as the second lever arm, a lever arm which is shorter than the actuating lever arm and which carries the bearing connection section of this lever element, and wherein the second lever element has a long first lever arm, which carries the bearing connection section of this lever element and which is longer than the lever arm that carries the bearing connection section of the first lever element, and has a second lever arm, which is shorter than its first lever arm and which moves the locking means. The lever arrangement may form a knee lever which, when actuated to move the locking means into the locking position, can be moved beyond a dead center and latches there. In further aspects, the invention specifies a medical, particularly surgical, instrument which is formed from a tool holder and grip according to the invention and from a medical, particularly surgical, tool which is connected thereto. Finally, a further aspect of the invention is to be seen in a set for forming a medical, particularly surgical, instrument which consists of a tool holder and grip according to this invention and at least two different medical, particularly surgical, tools.

Within the meaning of this invention, a "medical, particularly surgical, tool" is to be understood to mean not only a tool in the narrower sense, that is to say a tool for working on endogenous materials, such as muscle tissue or bone, or for supplying a patient with provided resources, such as, for example, implants, bone screws or the like. This term is also intended to encompass, in particular, medical treatment elements which can be connected to such a holder and grip, for example implant components which can be placed or removed by means of such a tool holder and grip.

According to the invention, a novel tool holder and grip for detachably connecting to a medical, particularly surgical, tool has, in a manner corresponding to the prior art, firstly, a basic body and a lever arrangement of lever elements which are connected to one another and are each mounted pivotably on the basic body. The basic body can in this case be divided into a grip section, which serves for gripping and handling the tool holder and grip, and a connection section, at which the tool holder and grip is connected to the surgical tool and which to this end typically has suitable connecting structures or connecting means. To this end, there is provided in the connection section a locking means which can be moved from a release position into a locking position and which serves for locking a tool that is placed on the connection section. In the locking position, the locking means locks the tool accordingly, and in the release position the tool is released for detachment from the tool holder and grip.

Of the lever elements, a first has an actuating lever arm and a second moves the locking means, which in a preferred embodiment is formed on a lever arm of this second lever element. In this regard, the tool holder and grip according to the invention also corresponds in terms of its features to that known in the prior art from U.S. Pat. No. 6,663,636 B1. In a manner differing from the latter, the tool holder and grip according to the invention is now characterized in that the lever arrangement is formed of precisely two lever elements which, by virtue of pivot bearing sections formed thereon, are each arranged directly and removably, and in such a way as to be able to pivot with respect to the basic body, on pivot bearing structures formed in the basic body. Arranging the pivot bearing sections of the lever elements directly on the basic body means here that this takes place without any connecting means, that is to say without further connecting parts, such as, for example, bearing pins or the like, as are used in U.S. Pat. No. 6,663,636 B1. Instead, the pivot bearing sections formed on the lever elements are part of the lever elements themselves and are formed in such a way that they can be inserted in or placed on corresponding pivot bearing structures of the basic body and already thus form the pivot bearing connection. This is also configured in such a way that a detachable connection is obtained, so that the individual lever elements can easily be removed from the basic body and the pivot bearing connections can be released thereby.

The tool holder and grip according to the invention also differs from the known prior art according to U.S. Pat. No. 6,663,636 B1 in that the two lever elements each have a bearing connection section on one of their lever arms, which bearing connection sections, when the tool holder and grip is assembled, are connected to one another in a detachable and direct manner (that is to say, they can be suitably connected to one another in order to assemble the tool holder and grip) and work together to form a connection pivot bearing for the two lever elements, which is movable relative to the basic body. Here, too, a direct connection of the two bearing connection sections once again means a connection which is free of connecting means, that is to say manages without any further elements such as, for example, bearing pins introduced into bores or the like. Instead, the two bearing connection sections of the two lever elements are directly connected to one another and thus form the connection pivot bearing.

In particular, it is preferred here if, on the tool holder and grip according to the invention, the two lever elements are fixed to the basic body in that the lever elements with the bearing connection sections, which are first arranged individually with the pivot bearing sections on the pivot bearing structures in the basic body, are connected to one another in order to form the connection pivot bearing and in this way secure the lever arrangement. In this solution, in order to break down the tool holder and grip according to the invention, in reverse order, first the connection pivot bearing is separated, typically by overcoming a corresponding retaining force, the two bearing connection sections of the individual lever elements are detached from one another, and then the two lever elements with their pivot bearing sections can simply be detached from the pivot bearing structures of the basic body and removed.

As a result, therefore, a simple tool holder and grip is specified which, in the preferred case in which the locking means is directly connected to the second lever element, consists of only three parts in total and can easily be broken down into these three parts, which tool holder and grip is not only able to be broken down and assembled easily but, in the broken-down state, results in relatively large parts which, by virtue of a relatively simple structure, are particularly easy to clean and sterilize. The force transmission to the locking means and/or the movement of the locking means for locking an attached medical, particularly surgical, tool takes place in this case in a manner that is similar to and just as reliable as that in the prior art according to U.S. Pat. No. 6,663,636 B1.

Typically and advantageously, there is provided in the connection section of the tool holder and grip a further structure for the placement of a corresponding mating structure on the tool. At present, this pair of structures to be connected to one another is preferably formed by an attachment peg, which is formed in the connection section of the tool holder and grip in one piece therewith and cooperates with a corresponding peg hole on the tool. This peg is preferably of a cross-section differing from a circular shape in order to prevent rotation. In particular, this peg has a cross-sectional structure that is trapezoidal in terms of its basic shape, optionally provided with rounded short sides. Such a structure has the advantage that a tool that is to be placed thereon can be placed in only one specific orientation, so that assembly errors can be ruled out. The tool may in this case also have a corresponding receiving structure for receiving the locking means with which it cooperates in the locking position to securely lock the tool that has been placed thereon.

In one advantageous further development of the invention, it is provided that the bearing connection section on one of the lever elements has a circular cylindrical section which runs with its longitudinal direction transverse to the direction of extension of the lever arm on which it is arranged, and is fixed to said lever arm, in particular is formed in one piece therewith. In this combination, the bearing connection section on the other of the lever elements comprises a receiving fork which is formed in a fork base with a radius corresponding to a radius of the circular cylindrical section and is delimited by lateral legs. It can easily be seen that such an arrangement by joining together the two bearing connection sections results in a corresponding connection pivot bearing without further components being necessary for connection purposes or as a rotation axle. The formation with a circular cylindrical section and a corresponding receiving fork moreover brings about a defined reduction in pivotability to pivotability about a single axis, namely the longitudinal axis of the circular cylindrical section. In the assembled state of the connection pivot bearing, pivoting movements in other directions are suppressed or blocked by the legs delimiting the receiving fork.

According to another further development of this solution, the legs of the receiving fork are of unequal length, wherein the leg that transmits force during a closing movement of the lever arrangement, that is to say a movement which the latter executes when moving the locking means into the locking position, is the longer leg. In order to lock the tool, a relatively high locking force must be reliably applied to the locking element precisely in this movement direction, which leads to a corresponding loading of the detachable connection at the connection pivot bearing. Inadvertent detachment of the connection pivot bearing must also reliably be prevented in this movement direction. A longer design, and possibly also a thicker design in terms of the material thickness, of the force-transmitting leg is therefore advantageous.

Furthermore, according to another advantageous further development, the design of the bearing connection sections of the connection pivot bearing, formed by the receiving fork and the circular cylindrical section, may be predefined in that the legs of the receiving fork have an opening width at their free ends that is smaller than the diameter of the circular cylindrical section, and one of the legs is configured as a spring tongue. This is advantageously the leg which, during the above-defined closing movement of the lever arrangement, does not transmit the force but, rather, is relieved of force. In a design with legs of unequal length, as described above, therefore, this may be in particular the shorter leg. By virtue of such a design of the receiving fork, the circular cylindrical section that is introduced into the fork from the free end of the legs can be pushed into the fork, thereby displacing outward the leg configured as a spring tongue, and is then secured in the fork once its diameter has passed the outer free end of the leg configured as a spring tongue and this leg has sprung back into its rest position. In this way, the connection pivot bearing is secured against inadvertent detachment of the cooperating bearing connection sections and, with the lever elements inserted in the basic body and the connection pivot bearing joined together, the arrangement of the lever arrangement and the pivotable connection thereof to the basic body can be secured.

In another advantageous further development of the invention, it is possible that one of the lever arms of the lever elements on which the bearing connection sections are arranged, in particular the lever arm provided with the bearing connection section of the second lever element, which moves the locking element, is configured as a spring arm with a spring elasticity in a direction transverse to its longitudinal extension. In addition, a spring effect formed therein may help to make the connection pivot bearing detachable, but to keep it in the connected position counter to a spring force in an assembled connection of the bearing connection sections. Advantageously, the lever arm configured as a spring arm is curved in a direction opposite to the force which, during the closing movement of the lever arrangement, acts thereon.

Advantageously, the pivot bearing sections, which are detachably connected in the connection pivot bearing, and the lever elements are, as a whole, configured in such a way that, in the event of an overstretching of the lever arrangement, in particular in the event of an overextension in the course of the opening movement which the lever arrangement executes when moving the locking means into the release position, the pivot bearing sections can be separated and detached from one another by overcoming a retaining force. In this way, it is easy to separate this connection, after which the two lever elements, with their pivot bearing sections, can easily be detached from the pivot bearing structures of the basic body and can be removed. The retaining force must in this case be such that, during normal use, inadvertent detachment of the bearing connection sections is ruled out, even after repeated and multiple use. On the other hand, this retaining force must not be too great, so that an easy separation of this connection is possible even by physically less robust medical staff.

One possibility for mounting one or both lever elements on the basic body in a pivotable and detachable and also direct manner consists in forming a circular cylindrical section as a bearing section on the at least one lever element and forming, as a pivot bearing structure which cooperates therewith, a receiving channel in the basic body with a channel base that is curved in a radius corresponding to the radius of the circular cylindrical section. This receiving channel is open at one side with an opening width into which the circular cylindrical section can be introduced and thus can be placed onto the channel base for pivoting purposes.

Another possibility for detachably mounting a lever element on the basic body consists in that a U-shaped bearing channel is formed as a bearing section in the lever element and has a channel base curved in a radius, and the pivot bearing structure is embodied by a bearing pin which is fixedly arranged on the basic body and which has a radius corresponding to the radius of the channel base. Instead of a continuous bearing pin, a circular cylindrical section which is formed on the basic body may also be selected here, wherein the circumference of the circular cylinder must be selected such that the pivoting travel of the corresponding lever element can be ensured by a running of the channel base of the U-shaped bearing channel along the lever element. The U-shaped bearing channel is once again open at one side with an opening width which makes it easy to place this bearing channel on the bearing pin or a corresponding structure having a circular cylindrical section, without any further attachment elements or attachment means being necessary.

Advantageously, there is formed in a section of the basic body an at least partially continuous receiving slot, that is to say a receiving slot which breaks through this basic body at both sides, in which the lever elements are each received at least with parts of their structures, and wherein the pivot bearing structures for pivotably mounting the lever elements are arranged in the receiving slot. The lever arrangement is thus arranged with wide areas in the interior of the tool holder and grip. Typically, however, at least the actuating lever arm will protrude out of the receiving slot since this is to be operated by an operator, typically a doctor or a medical assistant (surgical assistant).

In order to prevent over-pivoting in the closing direction of the lever arrangement, stop means for limiting a lever travel of the actuating lever arm in the closing direction may advantageously be provided on the actuating lever arm and/or on the basic body.

In order to generate a sufficiently high locking force, which acts on the locking means, by means of the lever arrangement, it is advantageous if the lever elements are each formed as two-armed lever elements, wherein the first lever element has the actuating lever arm as the first lever arm and has, as the second lever arm, a lever arm which is shorter than the actuating lever arm and which carries the bearing connection section of this lever element. The second lever element carries its bearing connection section on a first, long lever arm which is longer than the lever arm that carries the bearing connection section of the first lever element, and furthermore has a second lever arm, which is shorter than its first lever arm and which moves the locking element, on which this locking element can advantageously be directly formed.

The lever arrangement may advantageously be configured in such a way that it forms a knee lever which, when actuated to move the locking means into the locking position, can be moved beyond a dead center and latches there.

For the different types of application, positioning structures or acting structures for further tools or implements may be formed on the basic body of the tool holder and grip according to the invention. For example, in the region of the grip section, an end which is thickened in a plate-like manner may be provided as a stop surface for a striking tool such as, for example, a hammer. Cutouts or depressions may also be provided for the positioning of a chisel-like striking aid.

The elements, the basic body and lever elements, may each be manufactured individually, but in particular altogether, from a biocompatible metal, for example stainless steel, wherein the basic body may be provided with a plastic sheath or a cover made of a different material in the region of the grip part, in order to improve the grip and haptics, which sheath or cover is with particular advantage fixedly connected to the base material of the basic body, for example is applied thereto by injection molding.

As already mentioned, a medical, particularly surgical, instrument, which consists of a tool holder and grip according to the invention as described above and a medical, particularly surgical, tool which is connected thereto, is also part of the invention. In this case, the tool may be, in particular, a medullary cavity rasp for the proximal end of a human femur.

Finally, as already mentioned in the introduction, a set for forming a medical, particularly surgical, instrument as specified above is also part of the invention, which set comprises a tool holder and grip as described above and at least two different medical, particularly surgical, tools. Here, different medical, particularly surgical, tools are to be understood to mean, on the one hand, tools having the same function (for example bone rasps for the proximal end of a human femur) which are shaped or dimensioned differently. Also meant, however, are tools of different functionality, for example rasps and gauges. Among the different medical tools, there may also be implant parts which can be grasped and placed by a tool holder and grip according to the invention.

BRIEF DESCRIPTION OF THE DRAWINGS

Further advantages and features of the invention will become apparent from the following description of an example embodiment with reference to the appended figures. In the figures.

WAY(S) TO IMPLEMENT THE INVENTION

The figures show, in schematic sketches, one possible example embodiment of a tool holder and grip according to the invention for a medical, particularly surgical, tool, shown in different views and states. The figures are in no way to scale, and moreover also do not show the full and detailed construction of a corresponding example embodiment. Rather, they are to be understood as sketches which illustrate the basic principles and the main structure of the example embodiment and indicate in more detail where features according to the invention are shown and are to be explained.

The invention will be explained in more detail below with reference to the figures and on the basis of the example embodiment shown therein, and will be described in one possible embodiment variant.

Figure 1:
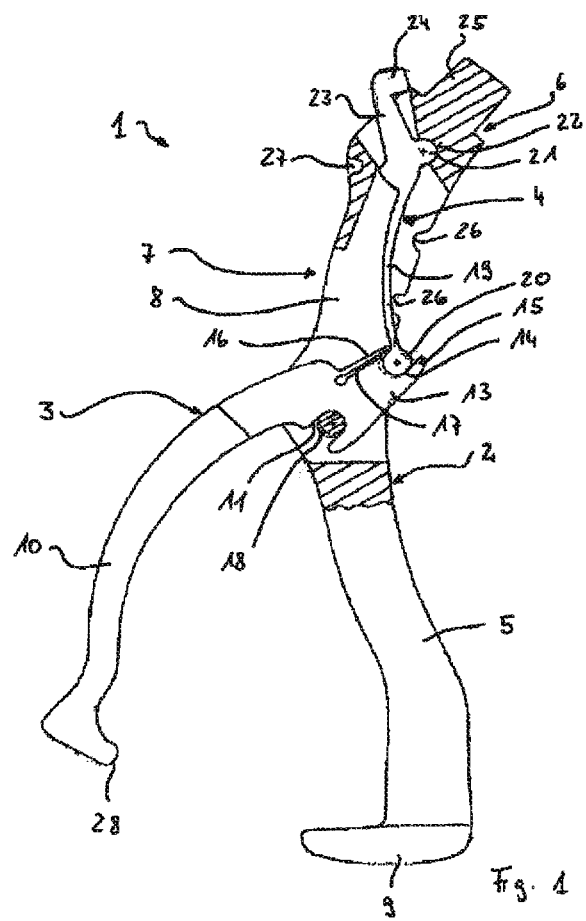
FIG. 1 shows a partially cut-away schematic side view of an example embodiment of a tool holder and grip according to the invention, without an attached medical tool and in the assembled state with the locking means in the release position.

Reference will first be made to FIG. 1 in order to describe the example embodiment. In said figure, a tool holder and grip configured according to the invention for a medical, particularly surgical, tool is denoted generally by reference numeral 1. Said tool holder and grip is formed of a basic body 2 and two lever elements 3 and 4, which are pivotably mounted on the basic body 2 and are connected to one another in an articulated manner and thus form a lever arrangement.

The basic body 2 has a grip section 5 and a connection section 6. The grip section 5 and the connection section 6 are connected in one piece with one another, wherein the basic body 2 and also the lever elements 3, 4 are formed in particular from a metal material, preferably from stainless steel. In a bearing section 7 located between the grip section 5 and the connection section 6, there is formed in the basic body 2 a receiving slot 8 which is formed at least partially in a continuous manner in a direction transverse to the longitudinal extension direction of the basic body 2. In the depiction of FIG. 1, the basic body 2 is shown in a partially cut-away manner, wherein the cut extends through the receiving section 6, the bearing section 7, and to an end of the grip section 5 facing towards the receiving section 6. The rest of the grip section 5 is shown without a longitudinal cut.

At an end of the grip section 5 located opposite the receiving section 6, there is a plate-like enlargement 9 which, on the one hand, delimits the grip section 5 and prevents any slipping of a hand gripping the grip section 2 in the direction of the end provided with the plate-like enlargement 9 and, on the other hand, serves as a striking face for applying sudden strikes, for example using a hammer-like tool, to the tool holder and grip 1. The grip section 5 of the tool holder and grip 1 is preferably provided, in a manner not shown in any greater detail here, with a coating or sheath, in particular made from a plastic or rubber, which improves the grip and haptics and is applied in particular by casting or injection molding.

The two lever elements 3, 4 each have two arms and are pivotably mounted, without further connecting or fastening means, in a direct and detachable manner on corresponding bearing structures of the basic body 2 and are directly and detachably connected to one another, likewise without further connecting means, in order to form a connection pivot bearing, as will be further described below.

A first lever element, the lever element 3, comprises an actuating lever arm 10 as the first lever arm. This actuating lever arm 10 serves for actuation of the lever arrangement by a person using the tool holder and grip 1 in a manner yet to be described below. This actuating lever arm 10 is the longer arm of the lever element 3. It extends as far as a pivot point of the lever element 3, which is defined by a U-shaped bearing channel 11 that serves as the bearing structure. This U-shaped bearing channel 11 has a channel base 12 in the shape of a segment of a circle (cf. FIG. 2). The second lever arm 13 of the first lever element 3 is formed starting from the bearing channel 11 on the opposite side of the actuating lever arm 10, which defines the pivot point of the lever. This lever arm 13 is a shorter arm than the actuating lever arm 10. At its end facing away from the bearing channel 11, the lever arm 13 has a bearing connection section in the form of a receiving fork 14. Like the bearing channel 11, this receiving fork 14 is provided with a cross section formed in the shape of a segment of a circle at the fork base. In the direction perpendicular to the plane of the drawing, the bearing channel 11 and the receiving fork 14 extend with a uniform cross section, so that the respective base, which is in the shape of a segment of a circle in cross section, forms a circular cylindrical section when viewed three-dimensionally.

The receiving fork 14 is delimited by a longer, stationary first leg 15 and a second, shorter leg 16. This second leg 16, on account of the slot 17 which releases it from the rest of the material of the lever element 3, is configured as a spring tongue with a spring elasticity in a direction transverse to its longitudinal extension and in the plane of the drawing of FIG. 1.

With the bearing channel 11, the first lever element 3 is placed onto a bearing pin 18 which is circular in cross section and is fixedly integrated in the bearing section 7 and forms a fixed component of the basic body 2. This bearing pin 18 acting together with the bearing channel 11, particularly the channel base 12 (cf. FIG. 2), forms the pivot bearing of the first lever element 3.

The second lever element 4 is likewise a two-armed lever element. A first lever arm 19 of this lever element 4 is the longer lever arm of this lever element 4 and is moreover longer than the second lever arm 13 of the first lever element 3. This lever arm 19 has a circular cylindrical section 20 at its outer end, which is integrally formed thereon and which forms a bearing connection section of the lever element 4. The lever arm 19 has a thickness smaller than the radius of the circular cylindrical section 20 and runs in a curved manner. The material thickness, further dimensions and choice of material of the lever element 4 in the lever arm 19 thereof are such that this lever arm 19 is elastically deformable, transverse to its longitudinal extension direction and in the plane of the drawing of FIG. 1, and can thus have a spring effect.

The lever element 4 has a bearing section 21 in the form of a further circular cylindrical section which is integrally formed on this lever element 4. With this bearing section 21, the lever element 4 sits in a pivotably mounted manner in a receiving channel 22, which is in the shape of a circular cylindrical section, that is to say is circular in radius when seen in cross section, and which is formed in a section of the basic body 2 that is located close to the connection section 6. The receiving channel 22 extends over a circumferential section smaller than 180°, so that the lever element 4 with its bearing section 21 can be inserted into and removed from the receiving channel 22. The bearing section 21 and the receiving channel 22 together define the pivot point of the lever element 4.

A second lever arm 23 of the lever element 4 extends toward a side of the bearing section 21 located opposite the first lever arm 19, and is shorter in length than the first lever arm 19. At its outer end, this lever arm 23 carries a locking peg 24 which is circular in cross section and which serves, in a manner that will be further outlined below, to lock a tool that is placed onto the tool holder and grip 1 in the connection section 6.

The two lever elements 3 and 4 are connected to one another in an articulated manner by a connection of the circular cylindrical section 20, which is introduced into the receiving fork 14 on the second arm 13 of the first lever element 3 and is arranged at the outer end of the first lever arm 19 of the second lever element 4, to said receiving fork 14. Here, an opening width of the receiving fork 14, which is determined by a spacing between the free ends of the legs 15 and 16, is smaller than the diameter of the circular cylindrical section 20. In this way, said connection is secured. Due to the spring elasticity of the second leg 16, configured as a spring tongue, the circular cylindrical section 20 can be pushed into the receiving fork 14 and removed therefrom, wherein a spring force of the spring tongue 16 must be overcome, which spring tongue is moved away by a suitable procedure and, when the circular cylindrical section 20 is introduced into the receiving fork 14, secures said section at the end in a latching manner by springing back into its starting position.

In the assembled lever arrangement as shown in FIG. 1, formed by the lever elements 3 and 4 connected to one another in an articulated manner, said lever elements form an arrangement which operates according to the knee lever principle. This is because the sum of the distance calculated from the center of the circle of the circular channel base formed in the receiving fork 14 to the center of the circle having the radius of the circular segment-shaped channel base 12 in the bearing channel 11 and of the distance from the center of the circular cylindrical section 20 to the center of the circular cylindrical section on the bearing section 21 is greater than the distance from the center of the circular cross section of the bearing pin 18 to the center of a circle that defines the radius of the receiving channel 22, which is circular in cross section. In order to compensate for this difference in distance, the lever arm 19 is formed in an elastic manner, as described above. During a closing movement, in which the actuating lever arm 10 is moved from the position shown in FIG. 1 toward the grip section 5 of the basic body 2, the lever arrangement moves in such a way that the lever arm 23 moves the locking peg 24 toward an attachment peg 25 formed in the connection section 6. During this closing movement, the lever arrangement is first stretched, thereby overcoming a retaining force by the elastic deformation of the first lever arm 19 of the second lever element 4, and then a dead center is passed so that, with the locking peg 24 pivoted into the locking position, the lever arrangement latches and, due to the spring force of the flexible lever arm 19, is blocked against inadvertently moving back into the open position. Only a deliberate opening movement, which overcomes the spring force of the lever arm 19, is able to move the locking peg 24 back out of the locking position into the open position.

It is also possible to see in FIG. 1 two positioning channels 26 and a blind hole 27, which are formed on the basic body 2 and serve for positioning a chisel-like strike-transmitting element so as to be able to transmit forces, brought about by suitable strikes, to the tool holder and grip 1 and thus to a tool attached thereto, for example so as to be able to drive said tool, in the case of a medullary cavity rasp as the tool, into the medullary cavity of a bone and to be able to release it again therefrom.

Finally, it is possible to see an extension 28 in the region of the outer end of the actuating lever 10, which points toward the grip section 5 and which, during a closing movement of the actuating lever 10, hits against a stop face of the grip section 5 and thus forms a stop for limiting any further closing movement of the lever element 3 and thus of the lever arrangement. It is thus possible, in particular, to prevent the situation whereby, in the event of "overclosing", the lever arrangement on the connection pivot bearing becomes detached.

Figure 2:
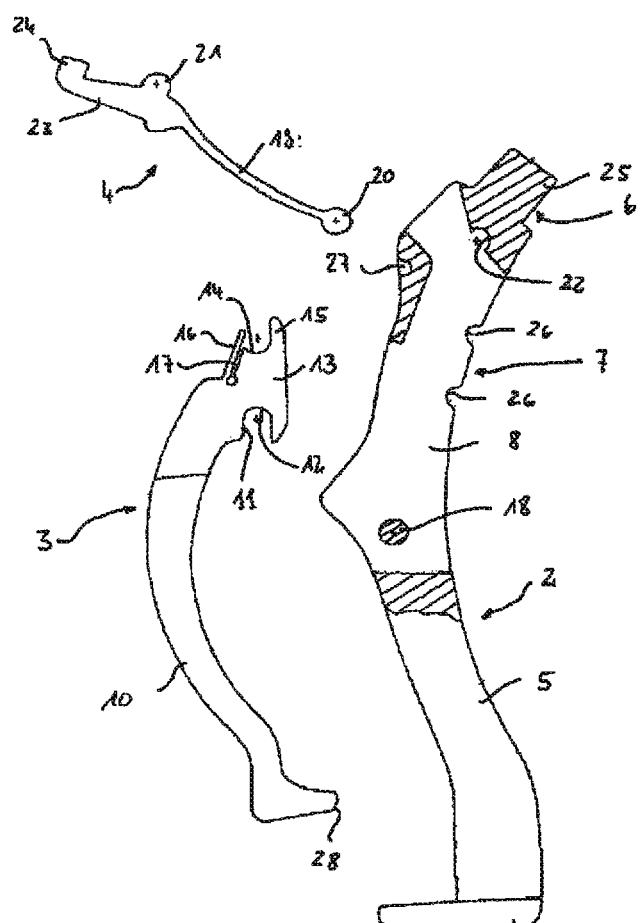
FIG. 2 shows a view of the tool holder and grip according to FIG. 1 in the broken-down state with a partially cut-away diagram of a section of the basic body.

In FIG. 2, the inventive tool holder and grip 1 of FIG. 1 is shown in a state broken down into its three individual parts, namely the basic body 2, the first lever element 3 and the second lever element 4. These three parts are the only parts obtained when the tool holder and grip 1 is broken down; in particular, there are no further connecting elements or other small parts. With regard to the individual parts and elements of the three individual parts, which are also provided with reference signs in FIG. 2, reference is made to the explanations given with regard to FIG. 1, which apply here in the same way. In particular, after use of the tool holder and grip 1, for example in the context of an orthopedic and/or surgical operation, said tool holder and grip can easily be broken down and the three parts (basic body 2, lever element 3, lever element 4) can easily be cleaned and sterilized in a quick and reliable manner. The tool holder and grip 1 can also then (as will be seen from the explanations below) easily be prepared again for the next use by assembling the three parts together.

Figure 3:
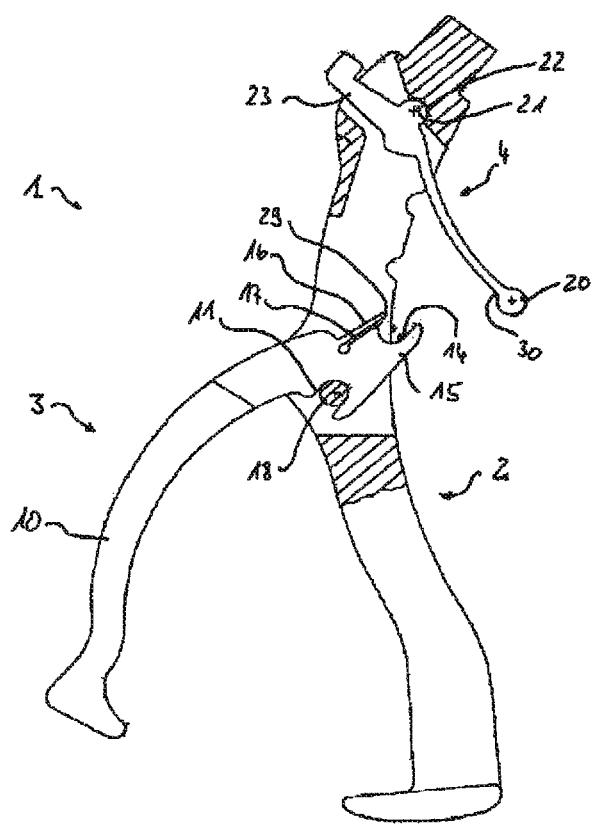
FIG. 3 shows a diagram of the tool holder and grip according to FIG. 1 with lever elements inserted in the basic body before these lever elements are connected to one another or after they have been detached from one another.

FIG. 3 shows a view—illustrated with a partially cut-away diagram of the basic body 2 as in FIG. 1 and FIG. 2—of the tool holder and grip 1 in a partially assembled or partially broken-down state. It can be seen here that the two lever elements 3, 4 are—already in the case of assembly or still in the case of breakdown—articulated on and inserted in the basic body 2 in order to form the respective pivot bearing. To this end, the first lever element 3 is placed with its bearing channel 11 onto the bearing pin 18. The second lever element 4 is inserted with its bearing section 21 into the receiving channel 22 on the basic body 2. Since the dimensions and opening widths of the bearing channels 11 and of the bearing channel 22 are such that the lever elements 3 and 4 can easily be guided with the bearing channel 11 over the bearing pin 18 and inserted with the bearing section 21 into the receiving channel 22, respectively, the assembly state shown in FIG. 3 can be achieved simply by bringing the lever elements 3 and 4 together with the basic body 2 and inserting them into the latter. At the time of breakdown, starting from the situation shown in FIG. 3, the lever elements 3 and 4 can easily be detached from the basic body 2 and removed.

In order to obtain the fully assembled state during assembly from the situation shown in FIG. 3, the connection pivot bearing, by which the two lever elements 3 and 4 are connected, must be formed and closed. To this end, the first lever element 3 and the second lever element 4 can be pivoted in such a way that the circular cylindrical section 20 is positioned between the ends of the legs 15 and 16, which delimit the receiving fork 14 on the first lever element 3. By applying a connecting force, the circular cylindrical section 20 is then pressed into the receiving fork 14, wherein the second leg 16 configured as a spring tongue is first pushed outward and then springs back into its starting position. In this way, the situation shown in FIG. 1 is obtained and is held in a latched manner.

When breaking down the tool holder and grip, the position shown in FIG. 3 is achieved in that the circular cylindrical section 20 is released from the receiving fork 14 by applying a release force which pushes outward the leg 16 configured as a spring tongue, and thus the connection of the lever elements 3 and 4 in the removed from the attachment peg 25.

It is also possible to see here once again how, in the release position, that is to say in the maximum opened state, the front end 29 of the leg 16 formed as a spring tongue bears against the transition edge 30. In the event of a further opening movement of the first lever element 3, the circular cylindrical section 20 is pushed out of the receiving fork 14 in a manner guided by the receiving fork 14 and the leg 15, wherein the leg 16 configured as a spring tongue is moved away. In this way, a separation of the connection pivot bearing can take place in order to release the connected lever arrangement and for a subsequent easy breakdown of the tool holder and grip 1 by simply removing the two lever elements 3, 4.

Figure 4:
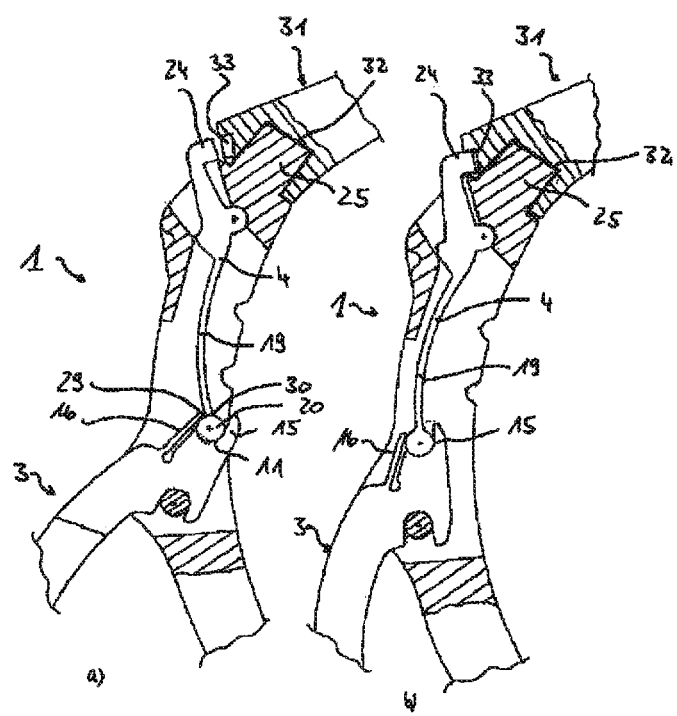
FIG. 4 shows, in two views, a and b, partially cut-away diagrams of part of the tool holder and grip according to FIG. 1, with a medical tool placed thereon in a released position (FIG. 4a) and in a locked position (FIG. 4b).

It is also clear here that the leg 15 in the receiving fork 14, which is thicker than the leg 16 in terms of the material thickness and which has no elastic spring properties, is the leg which transmits the force to the second lever element 4 at the time of closing or at the time of moving the locking peg 24 into the locking position shown in FIG. 4b. It can also be seen that the curvature of the first lever arm 19 of the second lever element 4 runs in the direction opposite to that in which the closing force is transmitted from the first lever element 3 to the lever arm 19 of the second lever element 4.

In the position shown in FIG. 4b, in which the medical tool 31 is securely connected to the tool holder and grip 1, a medical instrument according to the invention is formed. The tool 31 may be, for example, a bone rasp, in particular a rasp for the medullary cavity of the proximal end of the femur. However, it may also be a different tool, wherein the term tool is also to be understood to mean implant parts or the like. A set according to the invention for forming a medical instrument is obtained when at least two different medical tools 31 are combined with a tool holder and grip 1.

LIST OF REFERENCE SIGNS

1 tool holder/grip
2 basic body
3 lever element
4 lever element
5 grip section
6 connection section
7 bearing section
8 receiving slot
9 plate-like enlargement
10 actuating lever arm
11 bearing channel
12 channel base
13 lever arm
14 receiving fork
15 leg
16 leg
17 slot
18 bearing pin
19 lever arm
20 circular cylindrical section
21 bearing section
22 receiving channel
23 lever arm
24 locking peg
25 attachment peg
26 positioning channel
27 blind hole
28 extension
29 front end
30 transition edge
31 medical tool
32 peg hole
33 locking peg hole

The invention claimed is:

1. A tool holder and grip for detachably connecting to a medical tool, which has a basic body with a grip section and a connection section for connecting to the medical tool, wherein a locking means which is movable from a release position into a locking position is provided in the connection section for locking the medical tool that is to be placed on the connection section, wherein the tool holder and grip further has a lever arrangement of lever elements which are connected to one another and are each mounted pivotably on the basic body, of which lever elements a first has an actuating lever arm and a second moves the locking means, said locking means being formed on a lever arm of the second lever element wherein the lever arrangement is formed of the first and second lever elements which, by virtue of pivot bearing sections monolithically formed thereon, are each arranged directly and removably, and in such a way as to be able to pivot with respect to the basic body on pivot bearing structures monolithically formed in the basic body, and each has a bearing connection section on one of their lever arms, which bearing connection sections are connected to one another in a detachable and direct manner and work together to form a connection pivot bearing for the first and second lever elements, which is movable relative to the basic body.

2. The tool holder and grip according to claim 1, wherein the bearing connection section on one of the lever elements has a circular cylindrical section which runs with its longitudinal direction transverse to the direction of extension of the lever arm on which it is arranged, and is fixed to said lever arm and in that the bearing connection section on the other of the lever elements comprises a receiving fork, which is formed in a fork base with a radius corresponding to a radius of the circular cylindrical section and is delimited by lateral legs.

3. The tool holder and grip according to claim 2, wherein the legs of the receiving fork are of unequal length, wherein the leg that transmits force during a closing movement of the lever arrangement, which the latter executes when moving the locking means into the locking position, is the longer leg.

4. The tool holder and grip according to claim 2, wherein the legs of the receiving fork have at their free ends an opening width that is smaller than the diameter of the circular cylindrical section, and wherein one of the legs is configured as a spring tongue.

5. The tool holder and grip according to claim 1, wherein one of the lever arms of the lever elements on which the bearing connection sections are arranged, is configured as a spring arm with a spring elasticity in a direction transverse to its longitudinal extension.

6. The tool holder and grip according to claim 5, wherein the lever arm configured as a spring arm runs in a curved manner in a direction opposite to the force which, during a closing movement of the lever arrangement, which the latter executes when moving the locking means into the locking position, force acting thereon.

7. The tool holder and grip according to claim 1, wherein the pivot bearing sections, which are detachably connected in the connection pivot bearing, and the lever elements are configured in such a way that, in the event of an overextension of the lever arrangement the pivot bearing sections are separable and detachable from one another by overcoming a retaining force.

8. The tool holder and grip according to claim 1, further comprising a circular cylindrical section formed as a bearing section on at least one lever element for pivotably mounting the lever element in a receiving channel of the basic body, which receiving channel forms the pivot bearing structure and has a channel base that is curved in a radius corresponding to the radius of the circular cylindrical section.

9. The tool holder and grip according to claim 1, further comprising a U-shaped bearing channel which is formed as a bearing section in at least one of the lever elements and has a channel base curved in a radius for pivotably mounting the lever element on a bearing pin which forms the pivot bearing structure, is fixedly arranged on the basic body and has a radius corresponding to the radius of the channel base.

10. The tool holder and grip according to claim 1, further comprising an at least partially continuous receiving slot, formed in a section of the basic body, for at least partially receiving the lever elements, wherein the pivot bearing structures for pivotably mounting the lever elements are arranged in the receiving slot.

11. The tool holder and grip according to claim 1, further comprising a stop means arranged on the actuating lever arm or on the basic body for limiting a lever travel of the actuating lever arm in a closing direction in which the locking means is moved into the locking position.

12. The tool holder and grip according to claim 1, wherein the first and second lever elements are each two-armed lever elements, wherein the first lever element has the one actuating lever arm as the first lever arm and has, as the second lever arm, a lever arm which is shorter than the actuating lever arm and which carries the bearing connection section of this lever element, and wherein the second lever element has a long first lever arm, which carries the bearing connection section of this second lever element and which is longer than the lever arm that carries the bearing connection section of the first lever element, and has a second lever arm, which is shorter than the second lever element's first lever arm and which moves the locking means.

13. The tool holder and grip according to claim 1, wherein the lever arrangement forms a knee lever which, when actuated to move the locking means into the locking position, is movable beyond a dead center and latches there.

14. A medical instrument, consisting of a tool holder and grip according to claim 1 and a medical tool which is connected thereto.

15. A set for forming a medical instrument according to claim 14, comprising a tool holder and grip and at least two different medical tools and the tool holder and grip detachably connects to one of the two medical tools and includes a basic body with a grip section and a connection section for connecting to the one of the two medical tools, wherein a locking means which is movable from a release position into a locking position is provided in the connection section for locking the selected medical tool that is to be placed on the connection section, wherein the tool holder and grip further has a lever arrangement of lever elements which are connected to one another and are each mounted pivotably on the basic body, of which lever elements a first has an actuating lever arm and a second moves the locking means, said locking means being formed on a lever arm of the second lever element wherein the lever arrangement is formed of the first and second lever elements which, by virtue of pivot bearing sections formed thereon, are each arranged directly and removably, and in such a way as to be able to pivot with respect to the basic body on pivot bearing structures formed in the basic body, and each has a bearing connection section on one of their lever arms, which bearing connection sections are connected to one another in a detachable and direct manner and work together to form a connection pivot bearing for the first and second lever elements, which is movable relative to the basic body.

16. The tool holder according to claim 1, wherein the tool holder and grip is detachably connected to a surgical tool.

17. The tool holder according to claim 2, wherein the circular cylindrical section which runs with its longitudinal direction transverse to the direction of extension of the lever arm on which it is arranged, is formed in one piece with said lever arm.

18. The tool holder according to claim 3 wherein the legs of the receiving fork have at their free ends an opening width that is smaller than the diameter of the circular cylindrical section, and wherein the shorter leg is configured as a spring tongue.

19. The tool holder and grip according to claim 5, wherein the lever arm provided with the bearing connection section of the second lever element which moves the locking element is configured as the spring arm with the spring elasticity in a direction transverse to its longitudinal extension.

20. The tool holder and grip according to claim 7, wherein the pivot bearing sections which are detachably connected in the connection pivot bearing, and the lever elements are configured in such a way that, in the event of an overextension of the lever arrangement during an opening movement thereof, which the latter executes when moving the locking means into the release position, the pivot bearing sections are separable and detachable from one another by overcoming the retaining force.

21. The medical instrument according to claim 14, wherein the medical instrument is a surgical instrument and the medical tool is a surgical tool.

22. The set according to claim 15, wherein the set is for forming a surgical instrument and comprises at least two different surgical tools.

23. The medical instrument according to claim 17, wherein the medical tool is a medullary cavity rasp for the proximal end of a human femur.

* * * * *